(12) United States Patent
Kiguchi et al.

(10) Patent No.: US 6,238,811 B1
(45) Date of Patent: May 29, 2001

(54) ELECTROMAGNETIC WAVE GENERATING COMPOSITE

(76) Inventors: Hiroshi Kiguchi, 770-97 Ochi-cho, Midori-ku, Chiba-shi, Chiba-ken; Hisasi Sakurada, 5-28, 6-chome, Hon-cho, Funabashi-shi, Chiba-ken; Kunio Kageyama, 1331 Kasama-cho, Sakae-ku, Yokohama-shi, Kanagawa-ken, all of (JP)

(*) Notice: Subject to any disclaimer, the term of this patent is extended or adjusted under 35 U.S.C. 154(b) by 0 days.

(21) Appl. No.: 09/247,083

(22) Filed: Feb. 9, 1999

(30) Foreign Application Priority Data

Feb. 27, 1998 (JP) .................................. 10-062007

(51) Int. Cl.$^7$ ..................................... B32B 9/00
(52) U.S. Cl. .................. 428/692; 427/127; 427/201; 428/332
(58) Field of Search .................................. 428/692, 332; 427/127, 201

(56) References Cited

FOREIGN PATENT DOCUMENTS

355066291A * 5/1980 (JP).

* cited by examiner

Primary Examiner—Bernard Pianalto
(74) Attorney, Agent, or Firm—Oblon, Spivak, McClelland, Maier & Neustadt, P.C.

(57) ABSTRACT

A electromagnetic wave generating composite capable of attaining modification of water and activation of a living thing, being simply inexpensively manufactured irrespective of any form thereof, and being effectively directed to a variety of fields such as medical applications, agricultural applications and the like. The composite is constituted by a combination of a semiconductor and a magnet.

9 Claims, 2 Drawing Sheets

ELECTROMAGNETIC WAVE GENERATING COMPOSITE

BACKGROUND OF THE INVENTION

This invention relates to an electromagnetic wave generating composite.

A living thing typically contains a large amount of water as high as about 60 to 90%.

It is commonly known that water has capability of dissolving a variety of materials therein, which are introduced into the living thing together with water, to thereby exhibit various functions. Water is one of important materials constituting a living thing and functions thereof are highly varied depending on the form of water present in the living thing. Water has a chemical formula represented by $H_2O$. However, this is applied to the case that water takes the form of water vapor. It is said that water is constituted of some aggregates when it is present in the form of liquid, as taught in "Water-A Comprehensive Treatise" edited by F. Franks, Vol. 1–7, Plenum, N.Y. (1972–1982) and "Wayer Science Review" edited by F. Franks, Vol. 1–4, Cambridge Univ. Press, Cambridge (1985–1989).

The number of aggregates constituting liquid water substantially affects dissolution and hydration properties of the water. To this end, various ways are attempted for activation of water. The ways include, for example, electromagnetic wave energy, electromagnetic energy, mechanical energy, radiation energy, sound energy, infrared energy, a treatment using ceramics, a treatment using natural stones, addition of minerals and the like. Thus, activation of water is conventionally carried out using energy, adsorption, addition, elution or the like.

The inventor made careful study on activation of water and as a result, the following fact was found. An electromagnetic wave is varied by cooperation of an electric field and a magnetic field, so that an electromagnetic wave which is unvaried, is flat and does not undulate does not exist. This is proved by the fact that an electrostatic field and magnetostatic field solely exist. For example, a thundercloud has an electrostatic field but is free of a magnetic field. Terrestrial magnetism has only a magnetostatic field without an electric field.

Also, impingement of light on a semiconductor generates electromotive force, leading to occurrence of an electrostatic field. A composite which is a combination of a semiconductor and a magnet generating a magnetostatic field permits concurrent generation of both an electrostatic field and a magnetostatic field. It was found that location of water in the electrostatic field and magnetostatic field permits the water to be modified in properties. The modification may be measured using magnetic resonance spectroscopy. See Shigeru Nakane "Discovery of Water" published by Kohrin Shuppan.

Also, such modification of water was revealed by nuclear magnetic absorption spectroscopy, X-ray diffraction, neutron diffraction and the like.

Water is a diamagnetic material having magnetic susceptibility of $0.720 \times 10^{-6}$ $cm^3/g$, so that a polarity somewhat exists in clusters of water aggregates which are said to be absolutely non-magnetized. The polarity is arranged in correspondence to a polarity opposite thereto by an electromagnetic wave generated by the composite or a potential in an electrostatic field. Also, it is modified by a magnetic effect of a magnetostatic field.

SUMMARY OF THE INVENTION

The present invention has been made while taking the notice of such facts as described above.

Accordingly, it is an object of the present invention to provide a composite which is capable of readily and inexpensively improving properties of water due to a combination of characteristics of an electric field and those of a magnetic field.

It is another object of the present invention to provide a composite which is capable of promoting vital power of a living thing containing a moisture.

In accordance with the present invention, an electromagnetic wave generating composite is provided. The electromagnetic wave generating composite is obtained by combining a semiconductor and a magnet with a material reduced in dielectric constant. The semiconductor used has an electric resistance of $10^{-12}$ to $10^{10}$ $\Omega cm^2$ and a negative temperature coefficient, has a trace amount of metal atoms and crystals dispersed therein, and exhibits a photoelectric effect, a hall effect and a rectification action. Two or more of such properties may be combined with each other. The semiconductors may include, for example, metal semiconductors such as Ge, Se and Si, semiconductors exhibiting electronic/electrical functions such as $TiO_2$, $ZrO_2$, $BaTiO_3$, $SnO_2$, ZnO, PZT, $\beta$-$Al_2O_3$, ZnO—$Bi_2O_3$ and $SiO_2$, fine ceramics such as SiC and $Si_3N_4$, organic semiconductors, and the like. The semiconductors may be solely used. Alternatively, two or more of the semiconductors may be combined together.

BRIEF DESCRIPTION OF THE DRAWINGS

These and other objects and many of the attendant advantages of the present invention will be readily appreciated as the same becomes better understood by reference to the following detailed description when considered in connection with the accompanying drawings; wherein.

DETAILED DESCRIPTION OF THE PREFERRED EMBODIMENT

Figure 1:
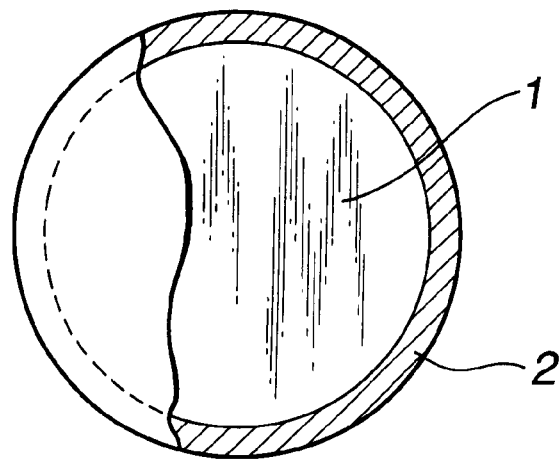
FIG. 1 is a partially cutaway front elevation view showing an embodiment of an electromagnetic wave generating composite according to the present invention.

Now, an electromagnetic wave generating composite according to the present invention will be described hereinafter with reference to the accompanying drawings.

A semiconductor constituting a part of an electromagnetic wave generating composite according to the present invention may be made of a metal oxide partially reduced under suitable conditions. Also, it may be made of a mixture of two or more metal oxides such as a mixture of $TiO_2$ and $SiO_2$, that of $TiO_2$ and $SiO_2$ and ZnO, or the like. Alternatively, it may be made of a combination or mixture of an metal oxide semiconductor and an organic semiconductor. The present invention is constituted by a combination of such a semiconductor with a magnet, resulting in exhibiting remarkable advantages. The magnet may be either a permanent magnet or an electromagnet. The permanent magnet has an advantage that it can be used without feeding it with an electric power and may be formed into a small size. Thus, it may be suitably used depending on a purpose thereof or applications thereof. The permanent magnet may be formed into any suitable shape such as a bar-like shape, a plate-like shape, a loop-like shape or the like depending on applications thereof. The semiconductor may be used in the form of a powder-like shape. Alternatively, it may be formed into either a shape like a thin film or a sheet-like shape in a manner to alternate with the magnet.

When the semiconductor is formed into a powder-like shape, it is preferably formed into a particle diameter of 1 mm or less. It is preferably fine as much as possible because of being increased in contact surface. It may have a binder added thereto, to thereby be formed into a sheet, a film, a coating or the like, which may be formed into a thickness of 1 mm or less.

Two or more kinds of semiconductors may be used in combination. In this instance, a combination of a p-type semiconductor and an n-type one exhibits an increased advantage. The combination permits junction substantially similar to p-n junction to be formed at contact points of the powders although it fails to form ideal p-n junction employed in the field of electronics. Electromotive force generated from the combination due to impingement of light thereon exhibits a function and an advantage rapidly as compared with use of a single semiconductor. The composite thus prepared fails to exhibit structural stability by itself. Thus, it may be encapsulated in glass, plastic or the like, resulting in being put to practical use.

Use of a material increased in dielectric constant does not substantially affect a magnetic field. However, it significantly affects an electric field, to thereby cause dielectric loss, leading to a failure to obtain energy from the magnetic field and electric field. This causes materials used therefor to be limited. Glass may be substantially used for this purpose. A plastic material may be suitably used unless it has a polar group. For the reason, high molecular hydrocarbons reduced in side chain such as polyethylene, polypropylene and the like are preferable. Also, polytetrafluoroethylene may be preferably used. Other high molecular materials having a dielectric constant of 4 or less and preferably 3.6 or less may be also conveniently used.

The invention will be understood more readily with reference to the following examples; however, these examples are intended to illustrate the invention and are not to be construed to limit the scope of the invention.

EXAMPLE 1

A powder of titanium oxide having a maximum particle diameter of 0.8 mm or less was partially reduced using hydrogen. The titanium oxide thus partially reduced had fine titanium particles formed on a peripheral surface thereof by reduction. The titanium oxide powder thus obtained was encapsulated in a glass tube together with the permanent magnet described above. The magnet was a ferrite magnet which was formed into a cylindrical shape of 4 mm in diameter and 80 mm in length. The cylindrical magnet was arranged in a glass container of 250 cc in volume while being covered with the semiconductor powder obtained by partial reduction.

Tap water was poured in the glass vessel having the composite received therein and then the glass vessel was closed with a cap. Then, the water was exposed to sun beams and subject to an experiment after one week, as follows:

Experiment 1

Water treated as described above and normal water or tap water untreated were provided. Also, 100 seeds of kaiware daikon was placed in each of the waters, to thereby examine germination of the seeds. The results were as shown in Table 1.

TABLE 1

(Number of Seeds Tested: 100)

|  | Number of germinating seeds | Germination ratio (%) |
|---|---|---|
| Treated water | 96 | 96 |
| Tap Water | 88 | 88 |

Experiment 2

Experiment 1 was substantially repeated, except that corn was substituted for kaiware daikon. The results were as shown in Table 2.

TABLE 2

(Number of Seeds Tested: 100)

|  | Number of germinating seeds | Germination ratio (%) |
|---|---|---|
| Treated water | 94 | 94 |
| Tap Water | 85 | 85 |

EXAMPLE 2

Example 1 was substantially repeated, except that titanium oxide (average particle diameter: 0.05 mm) partially reduced with hydrogen and silicon oxide (average particle diameter: 0.04 mm) were mixed at a ratio of 1:1. A germination ratio of kaiware daikon using the treated water was 99%.

EXAMPLE 3

Example 2 was substantially repeated, except that the titanium oxide and silicon oxide were mixed together at a ratio of 95:5 to 5:95. The germination ratios each were 99%.

EXAMPLE 4

Water treated with the same composite as used in Example 2, tap water, boiled tap water and commercially available mineral water were prepared. The waters each were placed in an amount of 100 ml in a beaker and an iron nail of 3 cm in length was immersed therein, resulting in occurrence of rust on the nail being observed. The results were as shown in Table 3, which indicates that the treated water substantially reduced occurrence of rust.

TABLE 3

|  | After 1 day | After 2 days | After 3 days | After 1 week | After 4 weeks |
|---|---|---|---|---|---|
| TW*1 | No change | No change | No change | Surface somewhat blackened | Blackened |
| TW*2 | Red rust slightly occurred | Increase in red rust | Further increase in red rust | Further increase in red rust | Red rust all over nail |
| BW*3 | No change | Red rust slightly occurred | Red rust somewhat increased | Further increase in red rust | Red rust all over nail |

TABLE 3-continued

|   | After 1 day | After 2 days | After 3 days | After 1 week | After 4 weeks |
|---|---|---|---|---|---|
| MW*4 | No change | Slight increase in red rust | Red rust somewhat increased | Further increase in red rust | Red rust all over nail |

*1Treated water
*2Tap water
*3Boiled water
*4Mineral water

EXAMPLE 5

A speed of growth of kaiware daikon after the germination was examined using the treated water, tap water and boiled water used in Example 4. The results were as shown in Table 4, which indicates that the treated water promoted the growth after germination as compared with the other waters.

TABLE 4

|  | After 1 day | After 2 days | After 3 days | After 4 days |
|---|---|---|---|---|
| Treated water | 3 cm | 6 cm | 12 cm | 15 cm |
| Tap water | 2 cm | 3.5 cm | 8 cm | 12 cm |
| Boiled water | 2 cm | 4.2 cm | 9 cm | 13 cm |

EXAMPLE 6

Figure 2:
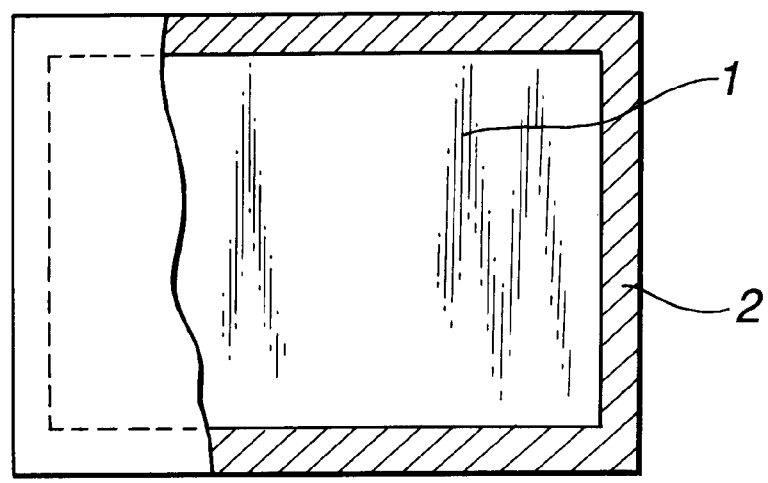
FIG. 2 is a partially cutaway side elevation view of the electromagnetic wave generating composite shown in FIG. 1.

Example 2 was substantially repeated, except that the same semiconductor as used in Example 2 was coated on a surface of a cylindrical magnet by means of an organic binder reduced in dielectric constant. The same results as Example 2 were obtained. Use of the semiconductor in the form of a film in place of a powder led to the same results. As shown in FIGS. 1 and 2, a permanent magnet 1 was coated on a surface thereof with a mixture obtained by mixing titanium oxide and silicon oxide with each other by means of a small amount of organic binder (one-pack type modified silicone), resulting in a semiconductor layer 2 being provided on the surface of the permanent magnet 1.

EXAMPLE 7

Figure 3:
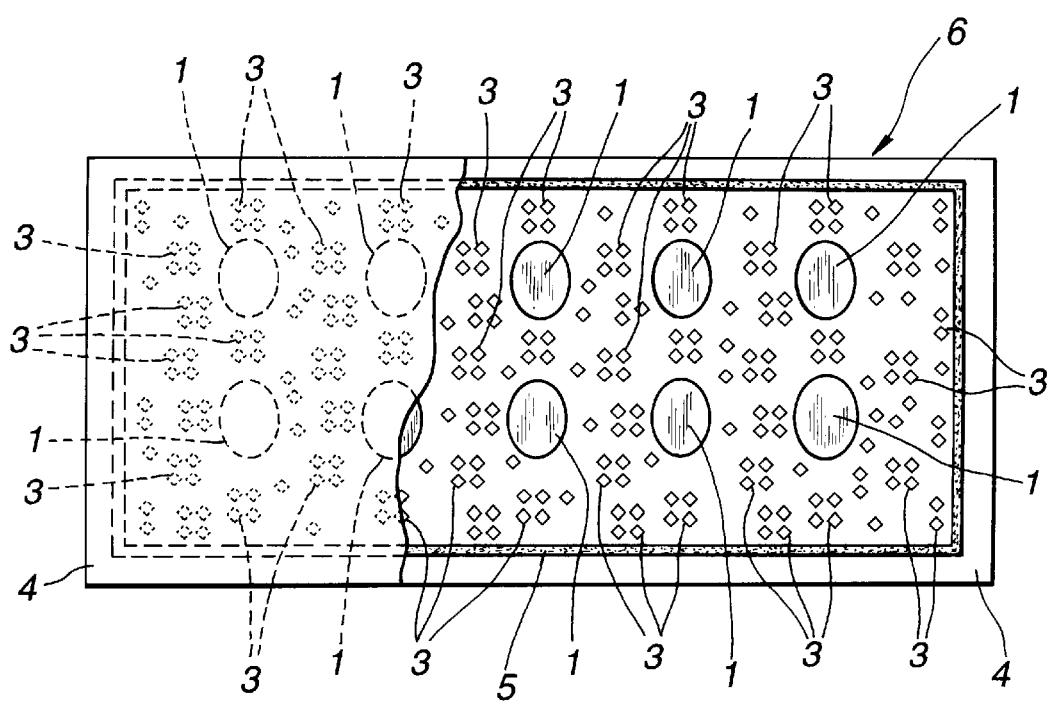
FIG. 3 is a schematic view showing arrangement of electromagnetic wave generating composites of the present invention heat-sealed in a polyethylene sheet.

As shown in FIG. 3, a permanent magnet 1 and a semiconductor 3 constituted of materials of three kinds or more were combined together to form an electromagnetic wave composite, which was then interposed between polyethylene sheets 4. Then, the polyethylene sheets were subject to heat sealing as indicated at reference numeral 5, to thereby be joined to each other, resulting in an electromagnetic wave generating composite/polyethylene sheet 6 being provided. Also, for comparison, a mere metal element and a pseudo-metal powder were combined together and then heat sealed in a polyethylene sheet, to thereby prepare an imitation polyethylene sheet. Then, the imitation polyethylene sheet was formed into the same configuration as the electromagnetic wave generating composite/polyethylene sheet 6. Then, the electromagnetic wave generating composite/polyethylene sheet 6 was applied to an affected part of each of ten of twenty subjects tired by physical exercise and the imitation polyethylene sheet was applied to the remaining ten subjects. After one day, the affected part of each of twenty subjects was examined.

As a result, it was reported that of ten subjects having the electromagnetic wave generating composite/polyethylene sheet 6 of the present invention applied thereto, one was somewhat decreased in fatigue and the remaining nine were relieved of fatigue.

Also, it was reported that of ten subjects having the imitation polyethylene sheet applied thereto, two were considerably decreased in fatigue, however, the remaining eight subjects were still tired.

EXAMPLE 8

A plastic magnet was formed into a circular sheet of 1.5 mm in thickness and 60 mm in diameter and then coated on a surface thereof with the semiconductor paste used in Example 6, resulting in a composite being prepared. Then, the composite was applied to a fatigued part of subjects while being wrapped in a cotton fabric. As a result, it was found that the composite exhibited a remedial effect as in Example 7.

EXAMPLE 9

Example 2 was substantially repeated, except that an electromagnet was substituted for the permanent magnet, resulting in a composite being prepared. The composite was placed in a glass vessel to treat tap water. Then, a germination ratio of kaiware daikon and a growth rate thereof were measured using the treated water. Results similar to those obtained using the permanent magnet were obtained. An electromagnet permits magnetizing force to be readily varied, to thereby be advantageously applied to a large-sized equipment for a medical service, agricultural production or the like.

As can be seen form the foregoing, the present invention provided a composite constituted of a combination of a semiconductor and a magnet. The semiconductor may be basically in the form of a powder and the magnet may be either a permanent magnet or an electromagnet. The composite of the present invention exhibits the same function and advantage also when the permanent magnet is made of a powder material into a solid structure by means of rubber, plastic or the like. Thus, the composite of the present invention attains modification of water and activation of a living thing and is simply inexpensively manufactured irrespective of any form thereof. Also, the composite of the present invention may be effectively directed to a variety of fields such as medical applications, agricultural applications and the like.

While a preferred embodiment of the invention has been described with a certain degree of particularity with reference to the drawings and examples, obvious modifications and variations are possible in light of the above teachings. It is therefore to be understood that within the scope of the appended claims, the invention may be practiced otherwise than as specifically described.

What is claimed is:

1. An electromagnetic wave generating composite consisting of semiconductor and a magnet, wherein the semiconductor comprises a p-type semiconductor powder and an n-type semiconductor powder mixed at a ratio of $95/5$ to $5/95$ by weight.

2. An electromagnetic healing device including the electromagnetic wave generating composite as defined in claim 1.

3. The electromagnetic wave generating composite as defined in claim 1, wherein said magnet is an electromagnet.

4. The electromagnetic wave generating composite as defined in claim 1, wherein said magnet is a permanent magnet.

5. The electromagnetic wave generating composite as defined in claim 1, wherein dielectric constant of said plastic sheet is 4 or less.

6. The electromagnetic wave generating composite as defined in claim 1, wherein said semiconductor and said magnet are sealed in a plastic sheet.

7. The electromagnetic wave generating composite as defined in claim 1, wherein said semiconductor and said magnet are sealed in a glass tube.

8. The electromagnetic wave generating composite as defined in claim 1, wherein said semiconductor powders are 1 mm or less in maximum diameter.

9. The electromagnetic wave generating composite as defined in claim 1, wherein said semiconductor consists of titanium oxide powder and silicon oxide powder.

* * * * *